US008277754B2

(12) United States Patent
Roumagnac et al.

(10) Patent No.: US 8,277,754 B2
(45) Date of Patent: Oct. 2, 2012

(54) SYSTEM FOR PRESSURE TREATMENT OF ARTICLES

(75) Inventors: Jean-Patrick Roumagnac, Le Coteau (FR); Francisco Naveros, Roanne (FR); Philippe Cocco, Roanne (FR)

(73) Assignee: Steriflow, Roanne (FR)

( * ) Notice: Subject to any disclaimer, the term of this patent is extended or adjusted under 35 U.S.C. 154(b) by 373 days.

(21) Appl. No.: 12/577,970

(22) Filed: Oct. 13, 2009

(65) Prior Publication Data

US 2011/0085947 A1    Apr. 14, 2011

(51) Int. Cl.
*B01L 3/00* (2006.01)
*B01L 99/00* (2010.01)
*A61L 2/00* (2006.01)
*A61L 9/00* (2006.01)

(52) U.S. Cl. ........................... 422/500; 422/297
(58) Field of Classification Search ............ 422/297, 422/500
See application file for complete search history.

(56) References Cited

U.S. PATENT DOCUMENTS

| | | | | |
|---|---|---|---|---|
| 3,895,911 A | * | 7/1975 | Prins | 422/302 |
| 4,170,421 A | * | 10/1979 | Balding et al. | 366/144 |
| 5,381,726 A | * | 1/1995 | Roumagnac et al. | 99/371 |
| 5,437,846 A | * | 8/1995 | Roumagnac et al. | 422/297 |
| 5,862,895 A | * | 1/1999 | Ricard | 188/289 |
| 6,867,393 B1 | * | 3/2005 | Lewis | 219/401 |

FOREIGN PATENT DOCUMENTS

EP    243213 A1 * 10/1987

OTHER PUBLICATIONS

Haegermark, Wenche Aale, "Shaken, not stirred",<http://www.nofima.no/mat/en/nyhet/2009/08/shaken-not-stirred>, Aug. 26, 2009, p. 1-3.*
English machine translation for EP 243213 A1 specification, Dec. 13, 2011.*
English machine translation for EP 243213 A1 claims, Dec. 13, 2011.*

* cited by examiner

*Primary Examiner* — Sam P Siefke
*Assistant Examiner* — Bryan Kilpatrick
(74) *Attorney, Agent, or Firm* — Alston & Bird LLP

(57) ABSTRACT

The purpose of the present invention is to propose a reliable, economically viable autoclave that also allows rapid heat treatment of food or pharmaceutical products in industrial quantities.
To this end, the subject of the invention is a system for shaking items, inside a device under pressure, comprising a chamber (100) equipped with a heating means (110) and with a pressurizing means (115), and a storage basket (200) for the items (P) coupled to a translational shaking means (300, 310-320-330-340), wherein the basket (200) is slidably mounted on a chassis (400) exhibiting a platform (410) supported by support columns (420) passing through the chamber (100) in a fluidtight and decoupled manner and intended to be secured to an immovable support (600).

20 Claims, 2 Drawing Sheets

SYSTEM FOR PRESSURE TREATMENT OF ARTICLES

Figure 1:
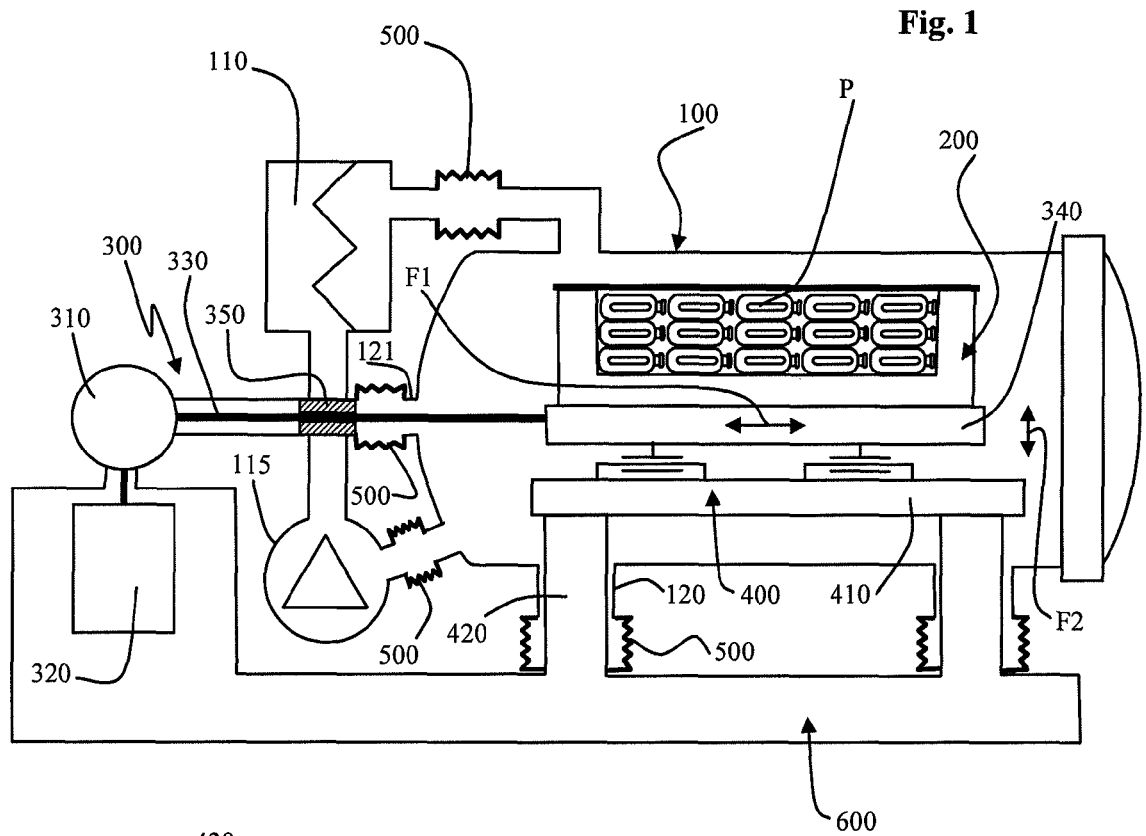

The invention relates to a system for shaking items inside a device under pressure, in particular an autoclave.

Numerous food and pharmaceutical products have to undergo a heat treatment (cooking, pasteurizing, sterilizing) in order to be sold. These may, for example, be liquid products such as milk-containing products, soups, purees, but may equally be solid products such as vegetables, meat, contained in various hermetic packagings such as cans, sachets, bowls, tubs.

The heat treatment needs to be able to be carried out uniformly over an industrial quantity of product. What is meant by an industrial quantity is a weight in excess of 100 kilos and, more specifically, a weight of one metric ton and more of product.

There are a number of systems currently known. The first is a static autoclave. This autoclave has a basket in which the products are stacked. The basket is then enclosed in the autoclave where it experiences a set increase in temperature and in pressure. For preference, superheated water may trickle over the products to encourage heat transfer.

This system has the advantage that industrial quantities of product (from 100 kg up to 10 metric tons) can be processed. Furthermore, it partially preserves the organoleptic qualities of the products, is reliable and repeatable.

This system requires a relatively long treatment time (of 2 to 3 hours). In addition, its implementation cooks the products.

In order to reduce the treatment time, a rotary system has been proposed, in which the basket is rotated in the autoclave during the heat treatment, at a frequency of 2 to 20 rotations per minute. This system reduces the treatment time because it encourages forced convection.

However, this system has a complex structure for rotating the basket. Furthermore, its reliability is not as good as the first system because numerous mechanical components become stressed and worn.

Another system, dubbed the "DALI", has been developed for mechanically shaking the products. This third system comprises a basket mounted on a translational system. The products are therefore shaken longitudinally, at a frequency of three return trips per minute, namely six jolts per minute.

An improved system, dubbed the "SHAKA", has been developed to allow hermetically packaged products to be shaken.

This system comprises an autoclave chamber in which there is positioned a basket connected to an eccentric by a linkage that emerges from the chamber. This mechanism allows the basket to be agitated at a frequency of 100 to 200 jolts per minute.

This system is highly effective because it allows sterilizing to be performed in a very short time, for example fifteen minutes. However, it is unable to agitate a significant quantity of product, at the very most it is able to agitate a few kilos to ten kilos or so. This is because the mechanical parts experience such vibration and impact stresses that industrial scale treatment with satisfactory reliability and for a reasonable cost becomes impossible.

It is therefore an objective of the present invention to propose a reliable, economically viable autoclave that also allows rapid heat treatment of food or pharmaceutical products in industrial quantities.

To do that, the invention proposes creating an autoclave that has a chamber that is flexibly decoupled, on the one hand, from an interior chassis supporting a basket and, on the other hand, from an external frame equipped with a mechanism for shaking the basket.

To this end, the subject of the invention is a system for shaking items, inside a device under pressure, such as an autoclave for the heat treatment of food or pharmaceutical products, comprising a chamber equipped with a heating means, with a pressurizing means, and a storage basket for the items coupled to a translational shaking means, in which system the basket is slidably mounted on a chassis exhibiting a platform supported by support columns passing through the chamber in a fluidtight and decoupled manner and intended to be secured to an immovable support.

By virtue of the shaking system according to the invention, it is possible to perform a short heat treatment on a significant quantity of products: About 15 minutes for a one metric ton basket. This weight corresponds to the weight of the items and of the actual basket itself. However, the ratio of the weight of the products to the weight of the basket depends on the type of packaging processed. If the articles are glass jars, there will be approximately 800 kg of items and 200 kg of basket; if the items are plastic tubs, then it is rather 600 kg of items and 400 kg of basket.

The weight of one metric ton is given by way of example.

According to other embodiments:
- the translational shaking means may comprise:
  - an eccentric that can be actuated by a motor, and
  - a shaft coupled to the eccentric and to the basket;
- the shaft may be supported by a bearing associated with the chamber in a fluidtight and decoupled manner;
- the shaft may be coupled to the basket by the intermediary of a stage slidably mounted on the chassis and of a securing means for securing the basket to the stage;
- the support columns may be secured to the chamber by means of a gaiter;
- the gaiter may be made of a material chosen from an elastomeric material and stainless steel;
- each gaiter may have a flexible tubular structure one end being secured to a column and the other end being secured to the chamber;
- the heating means and the pressurizing means may be associated with the chamber in a fluidtight and decoupled manner by means of a gaiter;
- the platform may be attached to the support columns by means of rods collaborating in a sliding manner with a hole formed in each column;
- the rods may be arranged on the platform such that they are coaxial with one or more favored direction(s) of expansion of the platform;
- the platform may have a substantially rectangular shape and the rods are arranged coaxially with respect to the diagonals of the rectangle;
- the return means may be arranged between the platform and the support columns in order to re-center the platform with respect to the support columns during cooling;
- the securing means may comprise a catching claw intended to collaborate with the basket and mounted to pivot relative to the stage between a position in which the basket is secured to, and a position in which the basket is released from, the stage;
- the catching claw may be combined with a return means encouraging return to the secured position; and/or
- the support columns of the chassis may be fixed to a frame external to the chamber.

Figure 2:
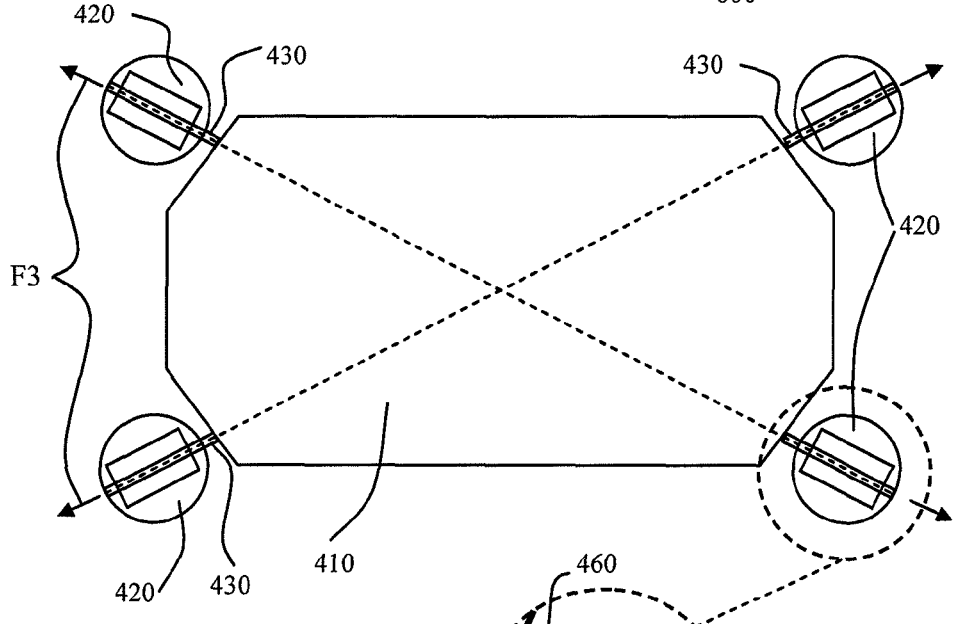
Figure 3:
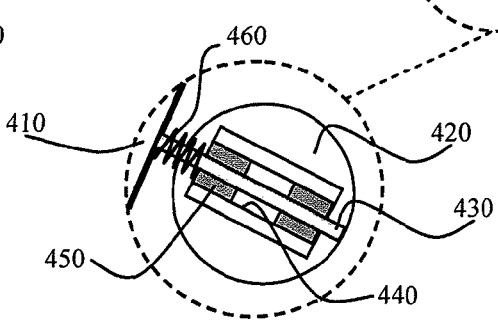
Figure 4:
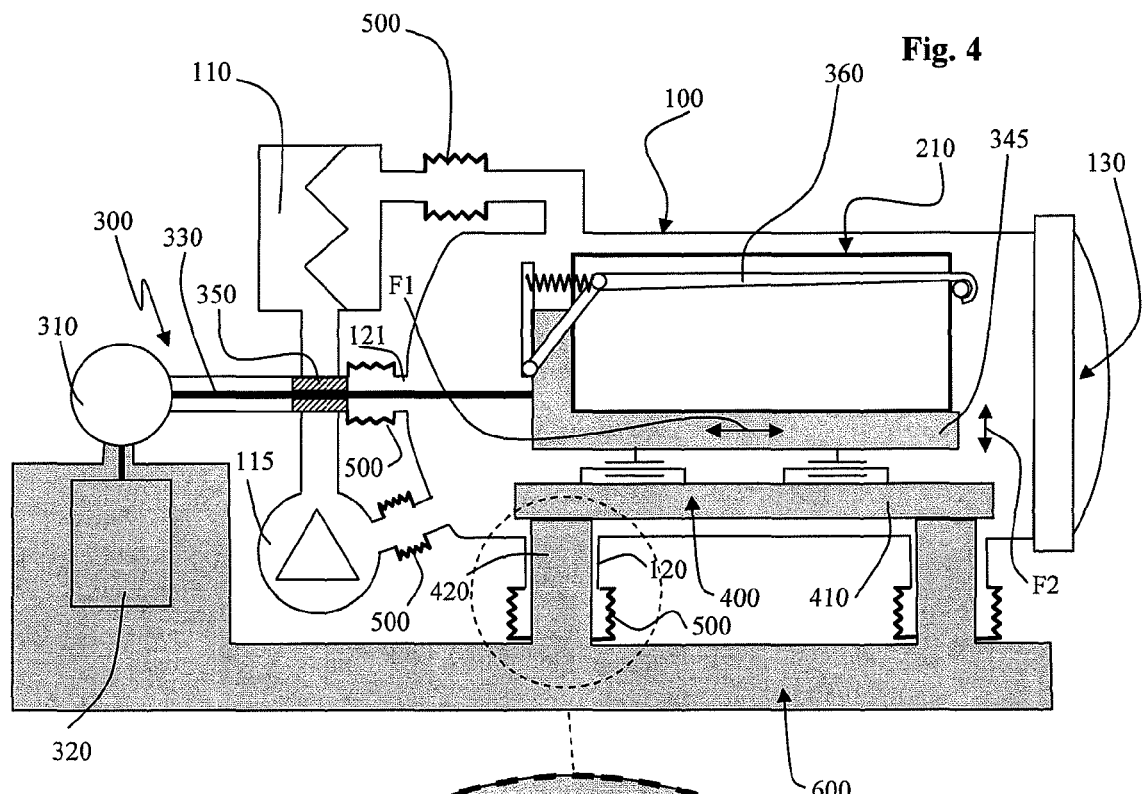
Figure 5:
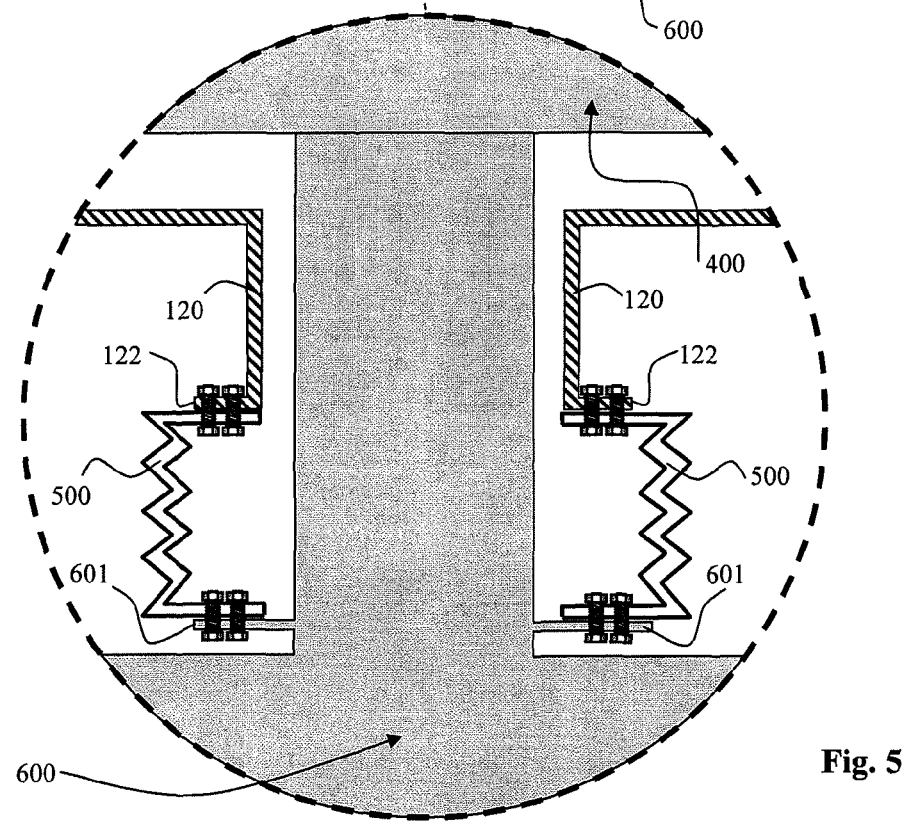

Other features of the invention will be listed in the detailed description which follows, which is given with reference to the attached drawings which, respectively, depict:

FIG. 1: a schematic sectioned view of a first embodiment of an autoclave according to the invention;

FIG. 2: a schematic plan view of one exemplary embodiment of an internal chassis according to the invention;

FIG. 3: a partial view of FIG. 2 illustrating the connection between the platform and the support columns of the internal chassis according to the invention;

FIG. 4: a schematic plan view of a second embodiment of an autoclave according to the invention; and FIG. 5: a partial view of FIG. 4 illustrating one embodiment of a fluidtight and decoupled attachment of the chamber to the chassis.

The invention relates in general to any device under pressure that undergoes vibrational or translational impact stresses. In the description which follows, the invention is described in respect of an autoclave, but is not in any way restricted thereto.

The invention relates in particular to an autoclave that allows the heating and pressurizing chamber to be decoupled from any mechanical assembly placed outside (known as the frame) and inside (known as the chassis). This decoupling makes it possible to avoid transferring to the chamber any vibrations and/or shocks experienced by the frame and/or by the chassis and which are generated by the translational shaking means. Furthermore, the autoclave according to the invention allows the various elements to expand independently of each other.

The embodiment illustrated in FIG. 1 comprises a chamber 100 equipped with a heating means 110 and with a pressurizing means 115. A storage basket 200 for the food or pharmaceutical products P is positioned inside the chamber 100. The basket 200 is coupled to a translational shaking means 300 and slidably mounted on an internal chassis 400 exhibiting a platform 410 supported by columns 420 intended to be secured to an immovable support such as a frame 600 that has a great deal of inertia. Thanks to the arrangement according to the invention, this frame, together with the chamber 100, can be designed and manufactured to the same requirements and the same tolerances as the chambers and frames of conventional machine tools.

The columns 420 of the chassis 400 pass through the chamber 100 in a fluidtight and decoupled manner.

To achieve this, the chamber 100 comprises tubular parts 120 surrounding the columns 420 with sufficient clearance that, in use, the columns 420 do not come into contact with the tubular parts 120. The latter have one end connected to a gaiter, for example made of an elastomeric material. Any material or structure which, through mechanical deformation, is able to absorb vibrations may be used. Each gaiter 500 has a flexible tubular structure 510, one end 520 being secured to a column 420 and the other end 530 being secured to the tubular part 120 of the chamber 100. Details of this structure are illustrated in FIG. 5.

In the embodiment of FIG. 5, the chamber 100 has a tubular structure 120 ending in a flange 122 for securing a gaiter 500, preferably made of an elastomeric material. The gaiter 500 is itself secured to a flange 601 welded to the column 420 or forming an integral part of this column. As an alternative, the gaiter 500 may be secured directly to the chassis 600.

In this way, the chamber 100 is suspended above and around the chassis 400. The latter therefore rests outside of the chamber without the risk of transmitting vibrations or impacts to the chamber. Further, the pressure and the heat inside of the chamber carry no risk of escaping thanks to the fluidtight connections between the chamber and the gaiters, on the one hand, and between the gaiters and the chassis or any other part (heating means, pressurizing means, shaking means or the like) on the other.

The shaking means 300 comprises an eccentric 310 that can be actuated by a motor 320, and a shaft 330 coupled to the eccentric 310 and to the basket 200.

In the embodiment of FIG. 1, the coupling between the shaft and basket is by way of a stage 340 to which the basket 200 is firmly secured by a securing means. The stage 340 is slidably mounted on the platform 410, for example by virtue of ball bearings or shoes made from a non-stick material.

For preference, the autoclave according to the invention comprises a bearing 350 to support the shaft coupled to the eccentric 310 and to the basket 200.

In general, the shaking means 300 is associated with the chamber 100 by means of a gaiter made of elastomeric material similar to the gaiter 500 described earlier.

In the embodiment of FIG. 1, the fluidtight and decoupled connection between the chamber 100 and the shaking means 300 is arranged between a tubular part 121 of the chamber 100 surrounding the shaft 330 and the bearing 350.

In use, the motor 320 actuates the eccentric 310 in such a way that the shaft 330 applies a reciprocating translational movement, in the direction of the arrow F1, to the basket 200.

If the mechanical connections between the motor 320, the eccentric 310 and the shaft 300 were perfect, that is to say free of any play, the movement transmitted by the shaft to the stage 340 would be a purely translational movement. However, in real life, there is always play in the various mechanical connections. Because of this play, the movement transmitted by the shaft 330 to the basket 200 is not a purely translational movement (solely in the direction of the arrow F1), and numerous vibrations in the direction of the arrow F2 are also generated.

Reducing this play would give rise to excessively high manufacturing costs. Further, this type of optimization tends to constrain all the assemblies in order to reduce as far as possible the stress levels, but does not make it possible to foresee a life that the users will find sufficiently long.

This is why heat treatment systems with translational shaking in the prior art have never been able to be implemented on industrial quantities of products. This is because if a one metric ton basket were shaken by the systems of the prior art, the vibrations would very soon cause the chamber to be destroyed, generating extremely hazardous thermal leakages.

The autoclave according to the invention allows decoupling between the shaking means and the chamber. Thus, the inevitable vibrations caused by the means of shaking the stage (by the geared motor units, the movement transmission systems, etc.) are not transmitted to the chamber, and it is possible to shake baskets 200 weighing in excess of one metric ton using components (chassis, frame and chamber) designed and manufactured to standard industrial requirements and tolerances. For example, the chamber may be manufactured using traditional sheet metalwork techniques, with no special requirements.

The chamber is designed and engineered to withstand various stresses:

Pressure,

Temperature,

The combination of the two: pressure and temperature,

The cyclic (batch) conditions which define their fatigue strength.

The mechanical decoupling between the chamber and the remainder of the autoclave system according to the invention does nonetheless generate problems of differential expansion between the parts of the autoclave that are hot and those which are at ambient temperature. Specifically, for example, the columns 420 have a "hot" part located inside the chamber, which is at a sterilizing temperature, and a "cold" part secured to the external frame 600 which is itself at ambient temperature.

During the heating and cooling phases, the various parts concerned, the chamber and the internal chassis, each expand and contract at a different rate (dependent on their heat transfer coefficient, their material, and therefore their expansion coefficient, etc.). The external frame itself remains at ambient temperature.

These differential expansions cannot be prevented. They therefore place the sheet metalwork structures (the chamber) and the all-welded structures (the frame) under stress.

FIG. 2 illustrates the means of the invention that solve the problem of differential expansion generated by the structure of the autoclave according to the invention.

In the embodiment illustrated in FIG. 2, the platform 410 is attached to the support columns 420 by means of rods 430 collaborating in a sliding manner with a hole formed in each column 420.

FIG. 3 is an enlarged view of this connection between the platform 410 and a column 420. In the embodiment illustrated in this enlargement, the hole 440, in which the rod 430 is engaged, is lined with a material 450 which allows sliding, with limited friction, of the rod 430 in the hole 440.

The securing rods 430 are arranged on the platform coaxial with one or more favored direction(s) of expansion of the platform. Specifically, depending on the shape of the platform, this platform will expand in one or more favored direction(s) of expansion.

In the embodiment of FIG. 2, the platform has a substantially rectangular shape. The vertices of the rectangle have been beveled to allow the rods to be inserted while at the same time optimizing space occupancy. The rods 430 are therefore arranged at the corners of the rectangle, coaxial to the diagonals of the rectangle, these diagonals embodying the favored directions of expansion of the platform.

During the heat treatment of the products P in the chamber 100, the platform undergoes differential expansion of the columns which, for their part, have a part inside the chamber 100 and another part at ambient temperature. During the expansion, the platform moves closer to the columns 420 and the rods 430 slide in the holes 440 in the direction of the arrows F3. As the temperature inside the chamber drops, the platform 410 contracts in the opposite direction to the arrows F3.

Advantageously, return means 460 are arranged between the platform and the support columns to re-center the platform with respect to the columns during cooling.

The embodiment illustrated in FIG. 4 has an advantageous means of securing the basket inside the autoclave.

In this embodiment, the basket 210 is positioned on a stage 345 equipped with a wedging edge 347. Furthermore, the basket 210 comprises a means 215 of grasping a catching claw 360. This catching claw 360 is pivot mounted about a shaft 362 coupled to the stage 345, between a securing position in which the claw is engaged with the grasping means 215, and a position in which the basket is released from the stage, in which position the basket 210 is free with respect to the claw. In order to hold and wedge the basket 210 on the stage (and against the wedging edge 347), the claw 360 is coupled to a return means 364.

In use, the basket 210 is introduced into the chamber 100 through an opening 130. The basket 210 is then positioned on the stage 345, preferably against the wedging edge 347. Next, the catching claw 360 is actuated to cause it to engage with the grasping means 215 of the basket 210. The claw 360 is then released and the return means 364 presses the basket against the wedging edge 347. The force and the structure of the return means 364 have to be chosen so that the translational shaking of the stage 345 is transmitted almost in its entirety to the basket 210 and to the products P it contains, thanks to the coupling between the claw and the basket.

The autoclave according to the invention eliminates all rigid and supposedly non-deformable connections between the external frame and the pressurized chamber, and between the internal chassis and the external frame, these being sources of deformation during the bringing-up to temperature and therefore sources of parasitic stresses leading to destruction of the device.

It is commonplace in industry to need to apply a movement to a part or to an assembly of parts while at the same time a heat treatment is being applied to this same part or assembly of parts.

More specifically, the part or parts may be containers, the movement allows the contents to which the heat treatment is applied to be agitated.

This is the case of cookers, pasteurizers or sterilizers in the agrifoodstuffs or pharmaceutical industries.

The movement applied is intended to accelerate the transfer of heat and/or to preserve the (organoleptic) qualities of the product contained.

Using the autoclave according to the invention, it is possible to carry out a short (15 minute) heat treatment on an industrial quantity of products.

The invention claimed is:

1. A system for shaking items inside a device under pressure, comprising a chamber equipped with a heating means and with a pressurizing means, and a storage basket for the items (P) coupled to a translational shaking means, wherein the basket is slidably mounted on a chassis exhibiting a platform supported by support columns passing through the chamber in a fluidtight and decoupled manner and intended to be secured to an immovable support.

2. The system for shaking items as claimed in claim 1, in which the translational shaking means comprises:
   an eccentric that can be actuated by a motor, and
   a shaft coupled to the eccentric and to the basket.

3. The system for shaking items as claimed in claim 2, in which the shaft is supported by a bearing associated with the chamber in a fluidtight and decoupled manner.

4. The system for shaking items as claimed in claim 2, in which the shaft is coupled to the basket by the intermediary of a stage slidably mounted on the chassis and of a securing means for securing the basket to the stage.

5. The system for shaking items as claimed in claim 1, in which the support columns are associated with the chamber by means of a gaiter.

6. The system for shaking items as claimed in claim 5, in which the gaiter is made of a material chosen from an elastomeric material and stainless steel.

7. The system for shaking items as claimed in claim 5, in which each gaiter has a flexible tubular structure, one end being secured to a column and the other end being secured to the chamber.

8. The system for shaking items as claimed in claim 1, in which the heating means and the pressurizing means are associated with the chamber in a fluidtight and decoupled manner by means of a gaiter.

9. The system for shaking items as claimed in claim 1, in which the platform is attached to the support columns by means of rods collaborating in a sliding manner with a hole formed in each column.

10. The system for shaking items as claimed in claim 1, in which the rods are arranged on the platform such that they are coaxial with one or more favored direction(s) of expansion of the platform.

11. The system for shaking items as claimed in claim 10, in which the platform has a substantially rectangular shape and the rods are arranged coaxially with respect to the diagonals of the rectangle.

12. The system for shaking items as claimed in claim 1, in which a return means are arranged between the platform and the support columns in order to re-center the platform with respect to the support columns during cooling.

13. The system for shaking items as claimed in claim 4, in which the securing means comprises a catching claw intended to collaborate with the basket and mounted to pivot relative to the stage between a position in which the basket is secured to, and a position in which the basket is released from, the stage.

14. The system for shaking items as claimed in claim 13, in which the catching claw is combined with a return means encouraging return to the secured position.

15. The system for shaking items as claimed in claim 1, in which the support columns of the chassis are fixed to a frame external to the chamber.

16. The system for shaking items as claimed in claim 6, in which each gaiter has a flexible tubular structure, one end being secured to a column and the other end being secured to the chamber.

17. The system for shaking items as claimed in claim 7, in which the heating means and the pressurizing means are associated with the chamber in a fluidtight and decoupled manner by means of a gaiter.

18. The system for shaking items as claimed in claim 17, in which the platform is attached to the support columns by means of rods collaborating in a sliding manner with a hole formed in each column.

19. The system for shaking items as claimed in claim 13, in which the securing means comprises a catching claw intended to collaborate with the basket and mounted to pivot relative to the stage between a position in which the basket is secured to, and a position in which the basket is released from, the stage.

20. The system for shaking items as claimed in claim 14, in which the support columns of the chassis are fixed to a frame external to the chamber.

\* \* \* \* \*